United States Patent [19]

Meilland

[11] Plant 4,868

[45] Jul. 20, 1982

[54] ROSE PLANT — MEIRILOCRA VARIETY

[75] Inventor: Marie L. Meilland, Antibes, France

[73] Assignee: Conard-Pyle Company, West Grove, Pa.

[21] Appl. No.: 191,133

[22] Filed: Sep. 26, 1980

[51] Int. Cl.[3] ..... A01H 5/00
[52] U.S. Cl. ..... Plt./15
[58] Field of Search ..... Plt./15

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which has attractive double flowers, few prickles, and a vigorous erect growth habit. The petals are buttercup yellow on the inside and tangarine orange on the outside and have a Chinese yellow unguis on the upper surface. The seed parent of the new variety was an unnamed variety and the pollen parent was of the MEILIMONA variety (U.S. Plant Pat. No. 4,013).

13 Drawing Figures

SUMMARY OF THE INVENTION

The object of the present invention is to provide a new variety of rose plant of the Hybrid Tea Class which is distinguished from prior varieties by the following characteristics:

(1) from a physical point of view the plant with bronze green adult wood is erect, forms double flowers having consistent petals which are buttercup yellow on the inside and tangerine orange on the outside with a Chinese yellow unguis on the upper surface, and bears few prickles; and (2) from the biological point of view the plant has vigorous vegetation, is highly susceptible to forcing, is not particularly susceptible to cryptogamic diseases, and forms flowers which last normally when cut having petals which drop off cleanly.

In view of these characteristics the new variety meets the needs of the horticultural industry for all purposes, and particularly is suited for the production of highly attractive cut flowers.

The new variety was created by artificial pollination whereby two parents which previously had been studied for the possible possession of the characteristics sought in the new variety were combined.

The seed parent was of an unnamed variety and the pollen parent was of the MEILIMONA variety (U.S. Plant Pat. No. 4,013). The parentage of the new variety may be expressed as follows:

UNNAMED VARIETY × MEILIMONA VARIETY.

The seeds resulting from the above pollination were sown and 69 plantlets were obtained which were physically and biologically different from each other. Selective study resulted in the identification of a single plant of the new variety. The desirable qualities of the new variety have been confirmed through extensive testing and the importance of the new variety has thereby been firmly established.

The characteristics and properties of the new variety obtained as indicated above are strictly transmissible by asexual propagation, e.g., by grafting a bud eye. The rose plant of the new variety has been designated the MEIRILOCRA variety.

BRIEF DESCRIPTION OF THE PHOTOGRAPH

The accompanying photograph shows as nearly true as it is reasonably possible to make the same in a color illustration of this character, typical specimens of plant parts of the new variety grown in a greenhouse at Cap d'Antibes, Alpes Maritimes, France, illustrated in:

FIG. 1 — a specimen of a young shoot;

FIG. 2 — a specimen of bud before the opening of the sepals;

FIG. 3 — a specimen of bud when the sepals burst open;

FIG. 4 — a specimen of a bud when the petals first open;

FIG. 5 — a specimen of a flower in the course of opening, plan view, upper surface;

FIG. 6 — a specimen of a fully opened flower, plan view, upper surface;

FIG. 7 — a specimen of a receptacle showing the arrangement of the stamens (sepals removed);

FIG. 8 — a specimen of a receptacle showing the arrangement of the pistils (stamens removed);

FIG. 9 — a portion of a flowering stem;

FIG. 10 — a portion of a main branch;

FIG. 11 — a specimen of leaf with three leaflets, upper surface;

FIG. 12 — a specimen of leaf with five leaflets, under surface; and

FIG. 13 — a specimen of leaf with seven leaflets, upper surface.

DETAILED DESCRIPTION

Figures 1, 2, 3, 4, 5, 6, 7, 8, 9, 10, 11, 12, 13:
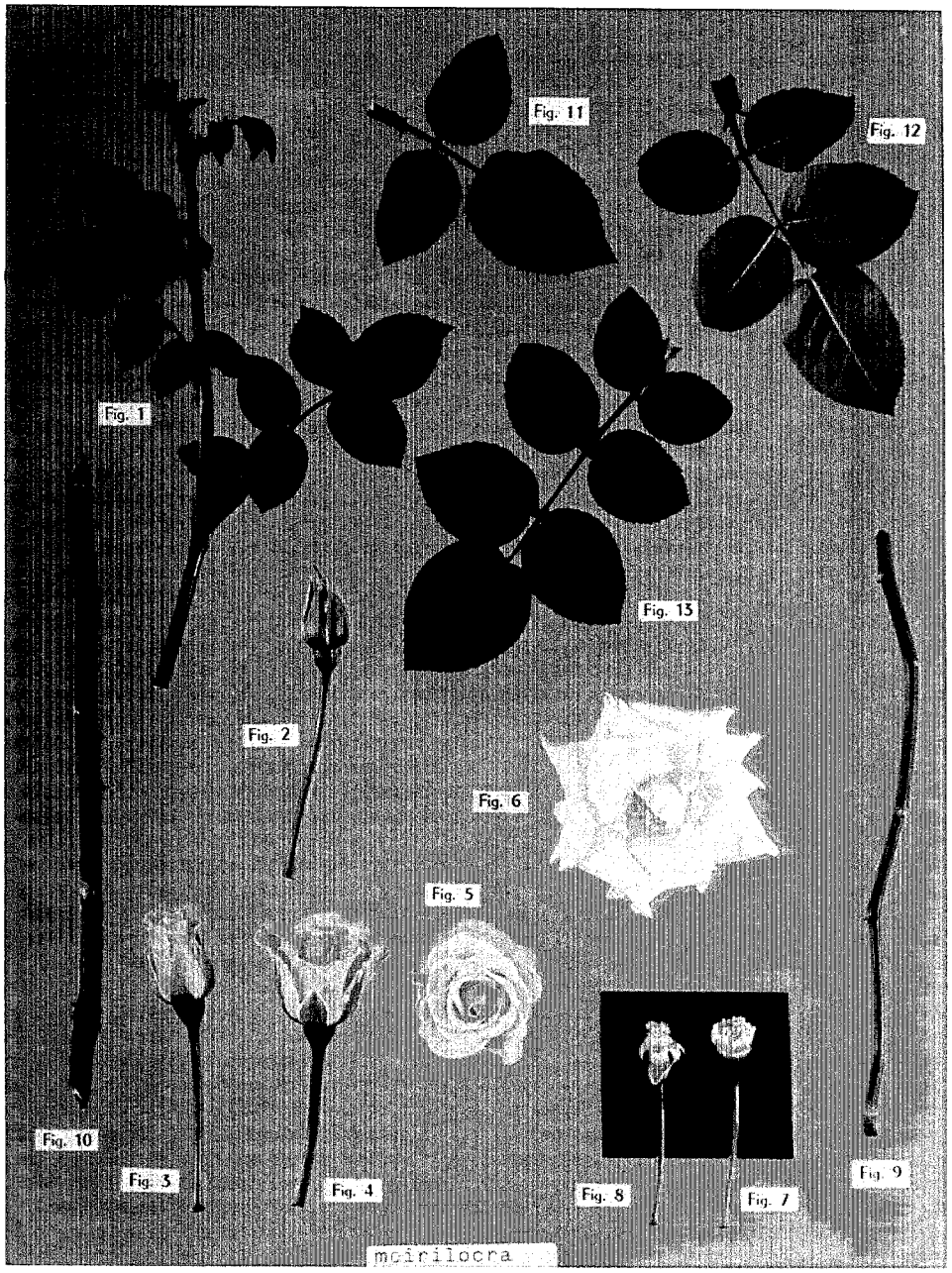

The plants described were grown in a greenhouse at Cap d'Antibes, Alpes Maritimes, France.

The chart used in the identification of the colors is that of the Royal Horticultural Society (R.H.S. Colour Chart). The terminology preceding the numbered references has been added to designate in common terms, the corresponding colors.

Class: Hybrid Tea.

Plant:

*Height.*—On plants pruned to approximately 0.85 meter the length of the flowering stems is approximately 60 to 65 centimeters.

*Habit.*—Erect.

Branches:

*Color.*—On young stems: bronze green 146/A (yellow-green group) more or less shaded reddish. On mature wood: bronze green 146/A (yellow-green group).

*Thorns.*—Shape: Upper edge: straight slightly inflected towards the base. Under edge: concave. Size: small. Quantity: very scarce. They are usually placed on the lower one third of the flowering branches. Color — on young stems: pink-greenish; — on mature wood: havana brown (common term).

Leaves:

*Stipules.*—Adnate, fairly strongly pectinated, fairly wide and linear.

*Petioles.*—Inner surface: grooved, reddish brown (young leaves), medium green (adult leaves), with edges more or less glandular and lightly tomentose. Outer surface: reddish green (young leaves), light green (adult leaves). It only very rarely bears a small crooked prickle.

*Leaflets.*—Number: 3-5-7 (most often), also 9. Shape: oval, with cordiform base and very pointed tip. Seration: simple and regular. Texture: leathery. General appearance: fairly ample foliage, fairly dense and semi-dull. Color: young foliage: upper surface: dark green 147/A (yellow-green group), but slightly lighter and edged reddish; under surface: bronze green 148/B (yellow-green group) largely maculated reddish. Color: adult foliage: upper surface: dark green 148/B (yellow-green group): under surface: bronze green 148/B (yellow-green group).

Infloresence:

*Number of flowers.*—Generally one flower per stem. However, upon forcing the first auxiliary eye below the flower sometimes may also blossom.

*Peduncle.*—Straight, rigid, lightly maculated reddish, and lightly tomentose.

*Sepals.*—Upper surface: tomentose and greenish. Under surface: light green, very slightly maculated reddish with tomentose edges (not glandular). The outside sepals have their edges very lightly appendiculated.

*Bud.*—Shape: oval. Length: approximately 3 cm. outside of the calyx at the opening of the sepals. Size: medium. Color: at point of opening: interior surface: tangerine orange 24/A (orange group) more or less suffused with nasturium 30/A (orange-red group) with wide unguis of Chinese yellow 16/A (yellow-orange group). Color — at point of opening — exterior surface: tangerine orange 24/B (orange group) more or less suffused with nasturium 30/A (yellow-orange group).

*Flower.*—Form: parallel sides, very well turbinated, double. Diameter: approximately 12 cm. on average. Color — at point of opening — upper surface: tangerine orange 24/B (orange group) more or less suffused with orange 30/D (orange-red group) with fairly wide unguis of Chinese yellow 16/A (yellow-orange group). Color — at point of opening — under surface: tangerine orange 24/C (orange group) more or less suffused with nasturium 30/A (orange-red group). Color — during course of opening: outside petals are tangerine orange 24/C (orange group) and inside petals are buttercup yellow 16/B (yellow-orange group). On upper surface the unguis is fairly wide and is Chinese yellow 16/A (yellow-orange group). Color — when fully open: outside petals are apricot 24/D (orange group) and inside petals are light yellow 16/D (yellow-orange group). Fragrance: light in flower vase. Lasting quality: normal in cut flower condition. Corolla — petals: texture: consistent; form: rounded; number: approximately 25 on average; stripping: they drop off cleanly. Stamens — number: approximately 173 on average. Anthers: yellow with orange edge. Filaments: orange-red, irregular in height. Pistils — number: approximately 110 on average. Stigmas: yellowish. Styles: free, straw with fuchsia tip, lightly twisted and tomentose. Receptacle: light green at the dehiscence of the anthers, and in longitudinal section it is narrow and in the shape of a jug.

Development:

*Vegetation.*—Vigorous.

*Blossoming.*—Continuous in greenhouse.

*Susceptibility to forcing.*—Great.

*Resistance to diseases.*—Good.

I claim:

1. A new and distinct variety of Hybrid Tea rose plant of vegetative reproduction characterized by the fact that:

from the physical point of view the plant with bronze green adult wood is erect, forms double flowers having consistent petals which are buttercup yellow on the inside and tangerine orange on the outside with a Chinese yellow unguis on the upper surface, and bears few prickles; and from the biological point of view the plant has vigorous vegetation, is highly susceptible to forcing, is not particularly susceptible to cryptogamic diseases, and forms flowers which last normally when cut having petals which drop off cleanly;

substantially as shown and described.

* * * * * mcirilocra